(12) United States Patent
Norasak

(10) Patent No.: US 10,206,426 B2
(45) Date of Patent: Feb. 19, 2019

(54) MAINTENANCE APPARATUS AND METHOD FOR VAPORIZING DEVICE

(71) Applicant: FUNAI ELECTRIC CO., LTD., Osaka (JP)

(72) Inventor: Sam Norasak, Lexington, KY (US)

(73) Assignee: Funai Electric Co., Ltd. (JP)

( * ) Notice: Subject to any disclaimer, the term of this patent is extended or adjusted under 35 U.S.C. 154(b) by 175 days.

(21) Appl. No.: 15/094,107

(22) Filed: Apr. 8, 2016

(65) Prior Publication Data

US 2017/0290369 A1 Oct. 12, 2017

(51) Int. Cl.
| | | |
|---|---|---|
| *A24F 47/00* | (2006.01) |
| *A61M 15/00* | (2006.01) |
| *A61M 15/06* | (2006.01) |
| *B05B 15/52* | (2018.01) |
| *B05B 15/50* | (2018.01) |
| *A61M 15/02* | (2006.01) |
| *A61M 11/04* | (2006.01) |

(52) U.S. Cl.
CPC .......... *A24F 47/004* (2013.01); *A24F 47/008* (2013.01); *A61M 15/0021* (2014.02); *A61M 15/025* (2014.02); *A61M 15/06* (2013.01); *B05B 15/50* (2018.02); *B05B 15/52* (2018.02); *A61M 11/041* (2013.01); *A61M 2209/10* (2013.01)

(58) Field of Classification Search
CPC ............ A61M 15/025; A61M 15/0021; A61M 2209/10; A61M 11/041; B41J 2/16535; B41J 2/16538; B41J 2/16544; A24F 3/02; A24F 9/04; A24F 9/06; A24F 9/08; A24F 9/10; A24F 9/12; A24F 47/008; A24F 47/004; B05B 15/02; B05B 15/0208

See application file for complete search history.

(56) References Cited

U.S. PATENT DOCUMENTS

| | | | |
|---|---|---|---|
| 4,911,181 A | | 3/1990 | Vromen et al. |
| 5,249,586 A | | 10/1993 | Morgan et al. |
| 5,548,310 A | * | 8/1996 | Binnert ............... B41J 2/16544 347/33 |
| 5,555,461 A | * | 9/1996 | Ackerman .......... B41J 2/16538 347/33 |
| 5,894,841 A | * | 4/1999 | Voges .................. A24F 47/008 128/200.14 |
| 5,946,009 A | * | 8/1999 | Youn ................... B41J 2/16547 347/22 |
| 5,954,979 A | | 9/1999 | Counts et al. |
| 6,116,247 A | | 9/2000 | Banyasz et al. |

(Continued)

FOREIGN PATENT DOCUMENTS

| | | | |
|---|---|---|---|
| JP | 2004283245 A1 | 10/2004 |
| JP | 4136741 B2 * | 8/2008 | .......... A61M 15/025 |

*Primary Examiner* — Seyed Masoud Malekzadeh
*Assistant Examiner* — Taryn Trace Willett
(74) *Attorney, Agent, or Firm* — Luedeka Neely Group, PC

(57) ABSTRACT

A maintenance apparatus for a fluid ejection and vaporization device and a fluid ejection and vaporization device containing the maintenance apparatus. The maintenance apparatus includes a movable wiper blade, the wiper blade being attached to an arm on one end of the arm, wherein a distal end of the arm is attached to an air operated mechanism for moving the arm and for causing a sweeping movement of the wiper blade over an ejection head in the fluid ejection and vaporization device.

13 Claims, 6 Drawing Sheets

(56) References Cited

U.S. PATENT DOCUMENTS

| | | | |
|---|---|---|---|
| 6,125,866 A | 10/2000 | Nichols et al. | |
| 6,517,187 B1* | 2/2003 | Dietl | B41J 2/16538 |
| | | | 347/33 |
| 8,975,764 B1 | 3/2015 | Abehasera | |
| 2003/0094187 A1* | 5/2003 | Maiwald | B05B 15/0208 |
| | | | 134/6 |
| 2004/0150690 A1* | 8/2004 | Childers | B05B 15/0208 |
| | | | 347/22 |
| 2007/0267031 A1 | 11/2007 | Hon | |
| 2008/0289653 A1* | 11/2008 | Dagsland | A61M 15/00 |
| | | | 134/8 |
| 2011/0175960 A1 | 7/2011 | Fukumoto | |
| 2013/0298905 A1 | 11/2013 | Levin et al. | |
| 2014/0345634 A1 | 11/2014 | Zuber et al. | |
| 2015/0027470 A1* | 1/2015 | Kane | A24F 47/008 |
| | | | 131/329 |
| 2015/0272216 A1* | 10/2015 | Dai | A61M 15/06 |
| | | | 131/328 |
| 2015/0343182 A1* | 12/2015 | Vazales | A61M 16/0463 |
| | | | 604/267 |
| 2017/0064997 A1* | 3/2017 | Murison | A24F 15/12 |
| 2017/0151806 A1* | 6/2017 | Kobayashi | B41J 2/17596 |
| 2018/0093050 A1* | 4/2018 | Stenzler | A61M 15/0013 |

\* cited by examiner

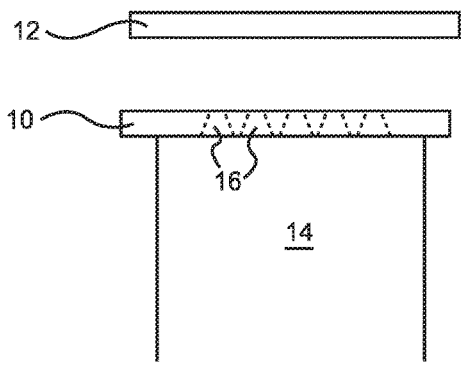
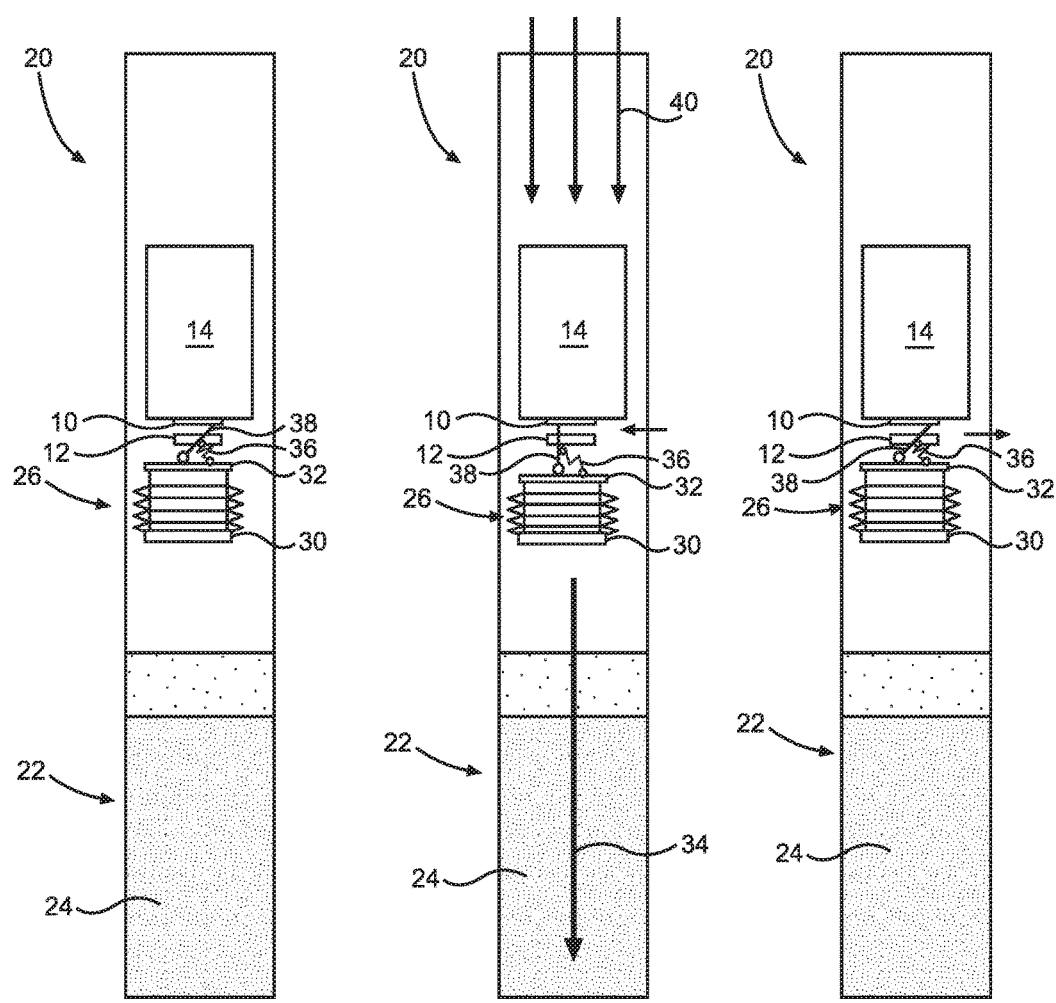
FIG. 1
FIG. 2　　FIG. 3　　FIG. 4

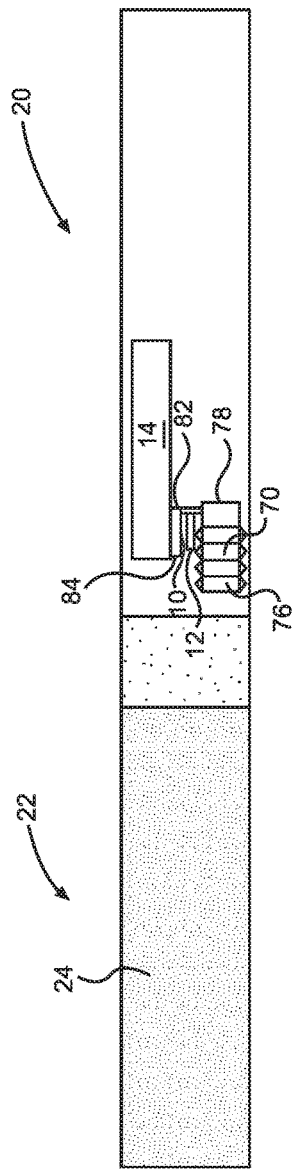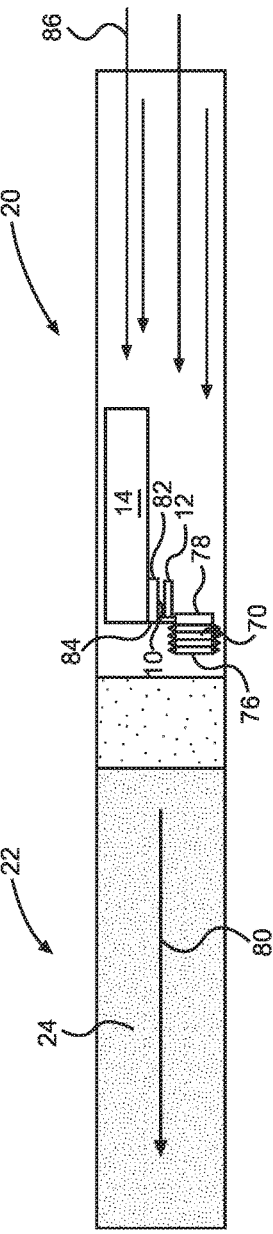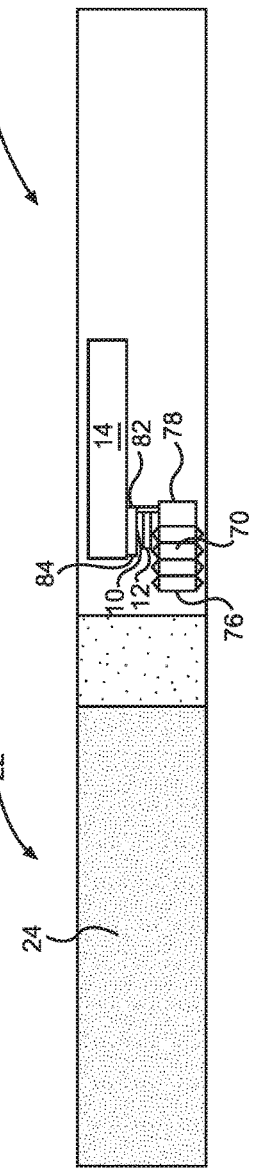

MAINTENANCE APPARATUS AND METHOD FOR VAPORIZING DEVICE

TECHNICAL FIELD

The disclosure is directed to fluid ejection and vaporization devices and a maintenance apparatus and method for fluid ejection and vaporization devices.

BACKGROUND AND SUMMARY

One of the applications of microfluidic ejection structures is to jet a solution on to another device where a secondary function may be performed. A common secondary function is to vaporize a solution using a heater such that the contents of the solution can be vaporized so as to deliver the solution as a gaseous substance. Applications of such technology include, but are not limited to, metering and vaporizing device for electronic cigarettes, vapor therapy, gaseous pharmaceutical delivery, vapor phase reactions for micro-labs, and the like. In all of these applications, a microfluidic ejection head is used to eject fluid onto a heated surface for vaporization of the fluid into a discharge conduit. For some applications, the fluids to be ejected have relatively low vaporization temperatures and thus can evaporate over time through ejection nozzles in the ejection head. For other applications, contamination of the ejection head between uses may be a problem. In some applications, the fluids may leave a residue on the ejection head that will, over time, inhibit the proper ejection of fluid from the ejection head or that may plug the ejection nozzles. Maintaining such devices so that precise fluid ejection is obtained is a problem due to the small size of such devices. Conventional maintenance devices for microfluidic ejection heads require a relatively large area for cleaning the ejection heads.

Accordingly, what is needed is a maintenance apparatus that can be operated to clean the ejection head in order to maintain proper ejection of fluid.

In view of the foregoing, an embodiment of the disclosure provides a maintenance apparatus for a fluid ejection and vaporization device. The maintenance apparatus includes a movable wiper blade, the wiper blade being attached to an arm on one end of the arm, wherein a distal end of the arm is attached to an air operated mechanism for moving the arm and for causing a sweeping movement of the wiper blade over an ejection head in the fluid ejection and vaporization device.

In another embodiment there is provided a method for maintaining the cleanliness of an ejection head in a fluid ejection and vaporization device having a source of air flow through the fluid ejection and vaporization device. The method includes providing, within the fluid ejection and vaporization device, a movable wiper blade, the wiper blade being attached to an arm on one end of the arm, wherein a distal end of the arm is attached to an air operated mechanism for moving the arm and for causing a sweeping movement of the wiper blade over an ejection head in the fluid ejection and vaporization device. A flow of air is caused to flow through the fluid ejection and vaporization device in an amount sufficient to cause movement of the wiper blade in a sweeping motion from a first position to a second position across the ejection head.

In some embodiments, the air operated mechanism is biased by a biasing device in order to return the wiper blade to the first position from the second position when the flow of air ceases.

In other embodiments, the air operated mechanism is selected from an air bladder, a spring bellows, and an air operated flapper.

In one embodiment, the air operated mechanism is an air operated flapper having a spring for biasing the air flapper to the first position.

In some embodiments, air is caused to flow through the fluid ejection and vaporization device by inhaling vapors generated by the fluid ejection and vaporization device.

In other embodiments, the wiper blade is disposed between an ejection head and a vaporizing heater in the fluid ejection and vaporization device.

In another embodiment, the air operated mechanism is disposed on a mouthpiece side of the vaporizing heater between the vaporizing heater and mouthpiece of the fluid ejection and vaporization device.

In some embodiments, the fluid ejection and vaporization device is an electronic cigarette.

BRIEF DESCRIPTION OF THE DRAWINGS

Other features and advantages of the inventive may be evident by reference to the following detailed description, drawings and claims wherein:

FIG. 1 is a schematic view of an ejection head for a fluid ejection and vaporization device according to the disclosure.

FIG. 2 is a side schematic illustration of a fluid ejection and vaporization device containing a cleaning apparatus according to a first embodiment of the disclosure, wherein a wiper blade of the cleaning apparatus is in a first position.

FIG. 3 is a side schematic view of the fluid ejection device according to the first embodiment of the disclosure, wherein the wiper blade of the cleaning apparatus is in a second position.

FIG. 4 is a side schematic view of the fluid ejection device according to the first embodiment of the disclosure, wherein the wiper blade of the cleaning apparatus has moved from the second position to the first position across an ejection head.

FIG. 12 is a side schematic view of a fluid ejection and vaporization device containing a cleaning apparatus according to a third embodiment of the disclosure, wherein a wiper blade of the cleaning apparatus is in a first position.

FIG. 13 is a side schematic view of the fluid ejection and vaporization device according to the third embodiment of the disclosure, wherein the wiper blade of the cleaning apparatus is in a second position.

FIG. 14 is a side schematic view of the fluid ejection and vaporization device according to the third embodiment of the disclosure, wherein the wiper blade of the cleaning apparatus has moved from the second position to the first position across an ejection head.

DETAILED DESCRIPTION OF EMBODIMENTS

Figure 5:
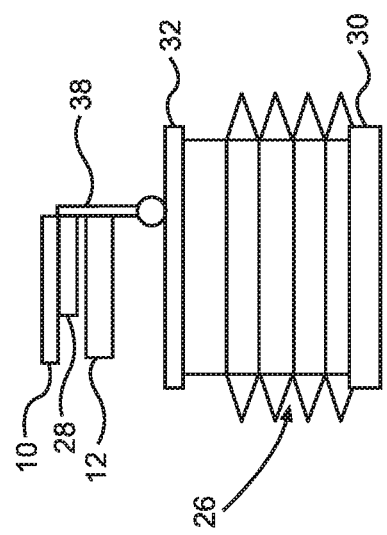
FIG. 5 is a side schematic view of a wiper blade and air operated mechanism according to the first embodiment of the disclosure.
Figure 6:
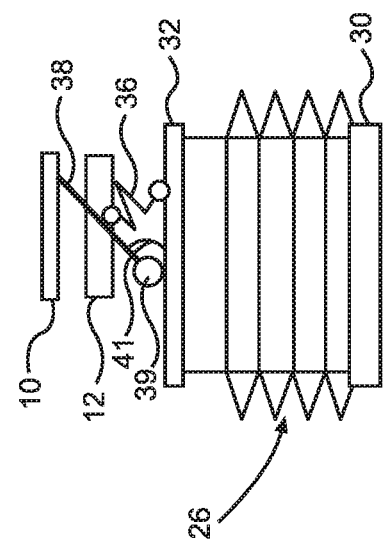
FIG. 6 is a front schematic view of a wiper blade and air operated mechanism according to the first embodiment of the disclosure.

The disclosure is directed to fluid ejection and vaporizing devices as schematically in FIGS. 2-4, 7-9 and 12-14 and maintenance apparatuses as shown schematically in FIGS. 5-6, 10-11 and 15-16. In all of the embodiment described herein, a fluid is ejected from an ejection head 10 (FIG. 1) onto a vaporization heater 12 wherein the fluid is vaporized and flows through a mouthpiece out of the fluid ejection and vaporization device. The fluid ejected from the ejection head 10 is provided by a fluid reservoir 14 through ejection nozzles 16 in the ejection head 10. The ejection head 10 may be a thermal microfluid ejection head or a bubble pump microfluid ejection head. Fluid ejection from the ejection head 10 is controlled so as to provide a predetermined amount of vapor to a user of the fluid ejection and vaporization device. In some embodiments, the fluid ejection and vaporization device is an electronic cigarette. In other embodiments, the fluid ejection and vaporization device may be a device for vapor therapy or for delivery of vaporized pharmaceutical compositions to a user. Regardless of the particular fluid ejection and vaporization device, the principal of operation of the maintenance apparatus is generally the same.

For example, with reference to FIGS. 2-6, a fluid ejection and vaporization device 20 according to a first embodiment of the disclosure is illustrated. Such devices 20 may be used for a wide variety of applications wherein a liquid is ejected by the ejection head 10 onto the vaporizing heater 12 to provide a vapor stream as described above with reference to FIG. 1. Such devices 20 are typically hand held devices such as electronic cigarettes that have a mouth piece 22 for inhaling vapors generated by the device 20. The mouthpiece 22 may include a vapor exit conduit 24 for flow of vapors out of the device 10. As described above, it may be necessary to remove debris and contaminants from the ejection head 10 so that the nozzles 16 of the ejection head 10 do not become blocked or restricted whereby fluid ejection is inhibited or reduced. However, the small size of the fluid ejection and vaporization device 20 makes it difficult to use any kind of conventional ejection head cleaning mechanism.

Accordingly, with reference so FIGS. 2-6, there is shown an air operated mechanism such as a bellows 26 or air bladder for moving a wiper blade 28 (FIG. 6) across the ejection head 10 from a first position illustrated in FIG. 2 to a second position illustrated in FIG. 3 when suction is applied to the mouth piece 22. In FIGS. 2-4, a first end 30 of the bellows 26 is fixed or stationary within the device 20, and a second end 32 of the bellows 26 is compressed toward the first end 30 of the bellows 26 in the direction of arrow 34 when suction is applied to the mouthpiece 22. A biasing device such as a spring 36 causes an arm 38 attached to the wiper blade 28 (FIG. 6) to move away from the second end 32 of the bellows 26 thus sweeping the wiper blade 28 across the ejection head 10 from the first position shown in FIG. 2 to the second position shown in FIG. 3. The arm 38 may be attached to the second end of the bellows 32 by a resilient connection such as rubber or thin plastic or a hinge 39. When suction is removed from the mouthpiece 22, the bellows 26 returns to an uncompressed state shown in FIG. 4 thus again sweeping the wiper blade 28 across the ejection head from the second position (FIG. 3) to the first position (FIG. 4). The ends 30 and 32 of the bellows 26 may be biased away from each other by an internal or external spring. Air movement through the fluid ejection and vaporization device 20 that causes the bellows 26 to compress is illustrated by arrows 40 (FIG. 3).

When the bellows is in the uncompressed state shown in FIGS. 2 and 4, the arm 38 is at an angle 41 of less than 90 degrees with respect to the second end 32 of the bellows 26, such as from about 20 to about 50 degrees, or from about 30 to about 45 degrees. When the bellows 26 is in the compressed state as shown in FIG. 3, the arm may be substantially perpendicular to the second end 32 of the bellows 26, such as an angle of from about 45 degrees to less than about 90 degrees with respect to the second end 32 of the bellows 26.

With reference to FIGS. 7-11, a second embodiment of the disclosure is illustrated. In the second embodiment, an air operated mechanism such as an air flapper 50 is used in the fluid ejection and vaporization device 20 instead of the bellows 26 described above. The ejection head 10, vaporization heater 12 and fluid reservoir 14 are described above and are disposed within the fluid ejection and vaporization device 20 as shown.

Figure 8:
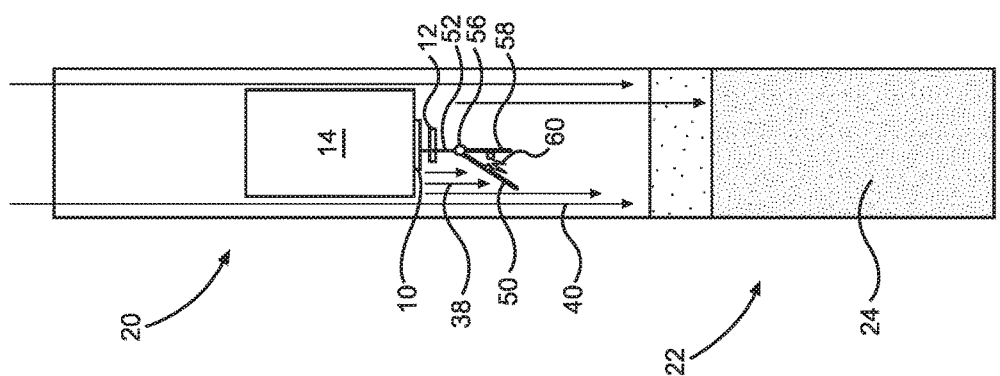
FIG. 8 is a side schematic view of the fluid ejection and vaporization device according to the second embodiment of the disclosure, wherein the wiper blade of the cleaning apparatus is in a second position.
Figure 7:
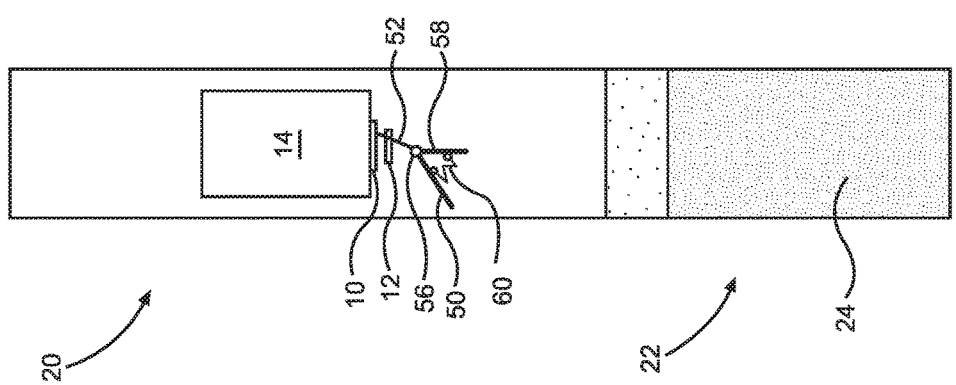
FIG. 7 is a side schematic view of a fluid and vaporization ejection device containing a cleaning apparatus according to a second embodiment of the disclosure, wherein a wiper blade of the cleaning apparatus is in a first position.
Figure 11:
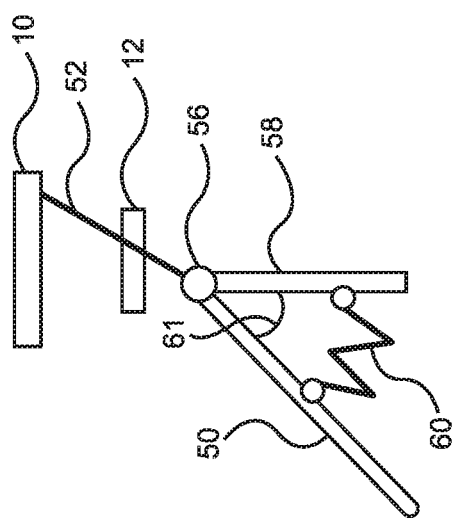
FIG. 11 is a side schematic view of a wiper blade and air operated mechanism according to the second embodiment of the disclosure.
Figure 10:
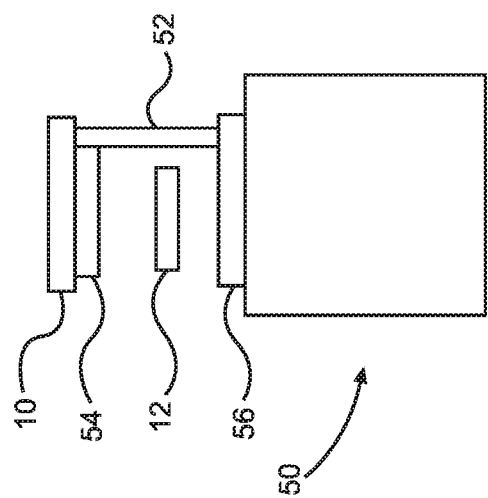
FIG. 10 is a front schematic view of a wiper blade and air operated mechanism according to the second embodiment of the disclosure.
Figure 16:
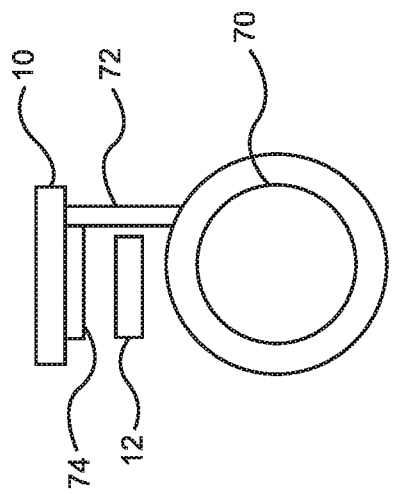
FIG. 16 is a front schematic view of a wiper blade and air operated mechanism according to the third embodiment of the disclosure.
Figure 15:
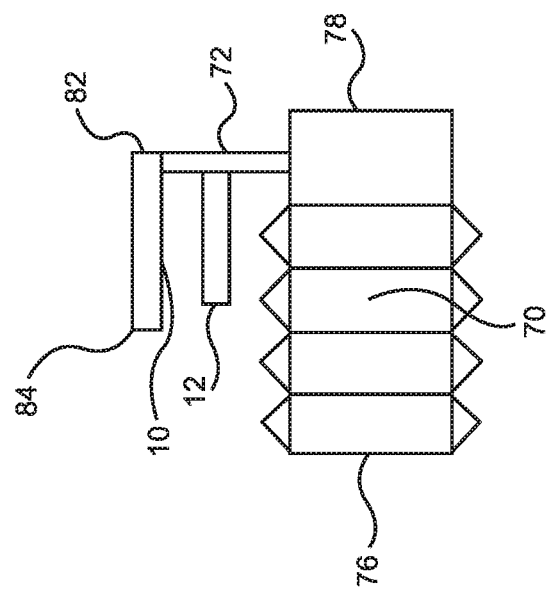
FIG. 15 is a side schematic view of a wiper blade and air operated mechanism according to the third embodiment of the disclosure.

In this second embodiment, the air flapper 50 has an arm 52 attached to a wiper blade 54 for moving the wiper blade 54 (FIG. 10) across the ejection head 10 from a first position illustrated in FIG. 7 to a second position illustrated in FIG. 8 when suction is applied to the mouth piece 22. The flapper 50 and arm 52 are attached by means of a hinge 56 to a support structure 58 within the fluid ejection and vaporization device. The hinge 56 enables pivotal movement of the flapper 50 and arm 52 relative to the support structure 58. A biasing devices such as weak spring 60 is disposed between the flapper 50 and support structure 58 to bias the air flapper 50 to the first position shown in FIGS. 7, 9 and 11. The air flapper 50 is disposed in an air flow path indicated by arrows 40 at an angle with respect to the support structure 58 so that it can move the wiper blade across the ejection head 10 when there is air flow through the fluid ejection and vaporization device 20. Accordingly, the air flapper 50 and arm 52 may be at an angle 61 ranging from about 25 to about 75 degrees relative to the support structure 58, such as from about 30 to about 50 degrees.

Figure 9:
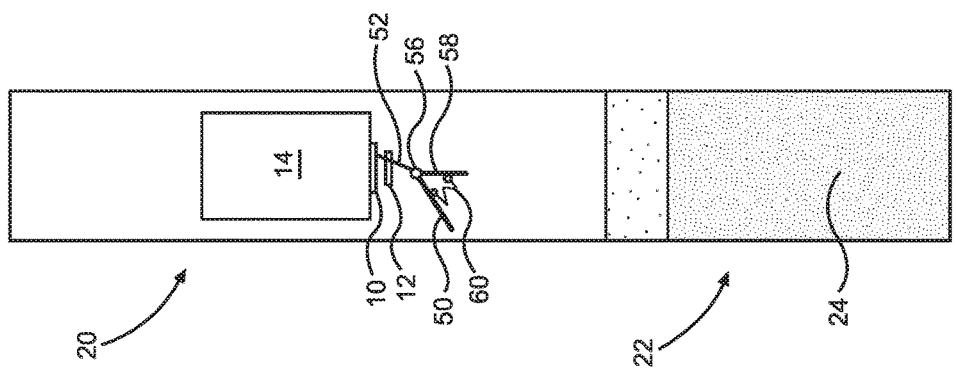
FIG. 9 is a side schematic view of the fluid ejection and vaporization device according to the second embodiment of the disclosure, wherein the wiper blade of the cleaning apparatus has moved from the second position to the first position across an ejection head.

Moving from FIGS. 7 to 9, the operation of the air flapper 50 is illustrated schematically. In FIG. 7, there is no suction on the mouthpiece 22 and thus no air flow through the fluid ejection and vaporization device 20. Therefore the wiper blade 54 is in the first position shown in FIG. 7. When suction is applied to the mouthpiece 22, air, indicated by arrows 40 is caused to flow through the fluid ejection and vaporization device 20 causing the air flapper 50 to move toward the support structure 58 thereby compression the spring 60 and moving the wiper blade 54 across the ejection head 10 as shown in FIG. 8. When the suction on the mouthpiece 22 is terminated, the spring 60 causes the air flapper 50 to move away from the support structure 58 causing the wiper blade 54 to move across the ejection head 10 in the opposite direction back to the first position as shown in FIG. 9. As the wiper blade 54 sweeps across the ejection head in both directions from the first position (FIGS. 7 and 9) to the second position (FIG. 8), debris and excess fluid are removed from the surface of the ejection head 10. The wiper blade 54 is made of a resilient material and will flex a sufficient amount to cause the wiper blade to remain in contact with the ejection head 10 regardless of the position of the wiper blade 54 in contact with the ejection head 10 in FIGS. 7-9. In the alternative, the arm 52 may flex as the wiper blade 54 moves across the ejection head 10 in the sequence of positions shown in FIGS. 7-9.

A third embodiment of the disclosure is illustrated in FIGS. 12-16. In this embodiment, the air operated mechanism is again a bellows 70 or bladder, however, compression of the bellows 70 causes lateral movement of an arm 72 attached to a wiper blade 74 (FIGS. 12-14) rather than angular movement of the arm 38 as shown in FIG. 5 in the first embodiment of FIGS. 1-6. Unlike the first and second embodiment, the third embodiment does not require the use of the biasing devices 36 and 60 of the first two embodiments. As with the first embodiment, the bellows 70 may include an internal or external spring or biasing device in order to return the bellows 70 from a compressed position to an uncompressed position.

In FIG. 13, a first end 76 of the bellows 70 is fixed or stationary within the device 20, and a second end 78 of the bellows 70 is compressed toward the first end 76 of the bellows 70 in the direction of arrow 80 when suction is applied to the mouthpiece 22. Accordingly, the bellows 70 is shown in a first uncompressed state in FIG. 12 wherein the wiper blade 74 is adjacent a first end 82 of the ejection head 10. When suction is applied to the mouthpiece 22, air movement through the fluid ejection and vaporization device as indicated by arrows 86, causes the bellows 70 to compress as shown in FIG. 13 there by sweeping the wiper blade 74 across the ejection head 10 from the first end 82 to a second end 84 of the ejection head 10. When suction is removed from the mouthpiece 22, the bellows 70 returns to an uncompressed state shown in FIG. 14 thus again sweeping the wiper blade 74 across the ejection head from the second end 84 (FIG. 13) to the first end 82 (FIG. 14).

As with the first embodiment, the ends 76 and 78 of the bellows 70 may be biased away from each other by an internal or external spring. Air movement through the fluid ejection and vaporization device 20 that causes the bellows 70 to compress is illustrated by FIG. 13.

It will be appreciated that the air operated mechanism of the third embodiment is simpler and has fewer moving parts than the air operated mechanism of the other two embodiments.

In all of the embodiments described herein, the fluid ejection and vaporization device 20 may be made from a wide variety of materials including plastics, metals, glass, ceramic and the like provided the materials are compatible with the fluids to be ejected and vaporized by the device 20. A particularly suitable material may be selected from polyvinyl chloride, high density polyethylene, polycarbonate, stainless steel, surgical steel, and the like. All parts, including the mouthpiece 22 that come in contact with fluids and vapors may be made of plastic. The wiper blade may be made of a resilient material such as an elastomeric material, natural rubber, fluoropolymer, and the like for wiping the ejection head 10. As with the other components of the fluid ejection and vaporization device the wiper blade should be made of a material that is resistant to the fluids used in and vapors generated by the fluid ejection and vaporization device 20.

In the first and third embodiments, the bellows may be made from a resilient material such as cloth, fiberglass, plastic and the like. The air flapper of the second embodiment may be made of rigid material such as metal or plastic.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fluid ejection and vaporization device comprising an ejection head, a vaporization heater for vaporizing fluid ejected from the ejection head and an apparatus for cleaning the ejection head, the apparatus comprising a movable wiper blade disposed between the ejection head and vaporization heater, the wiper blade being attached to an arm on one end of the arm, wherein a distal end of the arm is attached to an air operated mechanism for moving the arm and wiper blade in a sweeping motion over the ejection head, the air operated mechanism being selected from the group consisting of a spring bellows that is compressed when suction is applied to the fluid ejection and vaporization device and is uncompressed when suction is removed from the fluid ejection and vaporization device and an air operated flapper that pivots on a hinge as air flows through the fluid ejection and vaporization device, the air operated flapper having a biasing spring for causing the sweeping motion of the wiper blade over the ejection head when the air flow ceases through the fluid ejection and vaporization device.

2. The maintenance apparatus of claim 1 wherein the air operated mechanism comprises the spring bellows.

3. The maintenance apparatus of claim 1, wherein the air operated mechanism comprises the air operated flapper.

4. The maintenance apparatus of claim 3, wherein the spring of the air operated flapper biases the air flapper to a first position.

5. The maintenance apparatus of claim 1, wherein the air operated mechanism is operated by inhaling vapors generated by the fluid ejection and vaporization device.

6. The maintenance apparatus of claim 1, wherein the air operated mechanism is disposed on a mouthpiece side of the vaporizing heater between the vaporizing heater and mouthpiece of the fluid ejection and vaporization device.

7. The fluid ejection and vaporization device of claim 1 comprising an electronic cigarette.

8. A method for maintaining a cleanliness of an ejection head in a fluid ejection and vaporization device having a source of air flow through the fluid ejection and vaporization device and a vaporization heater for vaporizing fluid ejected from the ejection head, the method comprising: providing, within the fluid ejection and vaporization device, a movable wiper blade disposed between the ejection head and vaporization heater, the wiper blade being attached to an arm on one end of the arm, wherein a distal end of the arm is attached to an air operated mechanism for moving the arm and wiper blade in a sweeping motion over the ejection head, the air operated mechanism being selected from the group consisting of a spring bellows that is compressed when suction is applied to the fluid ejection and vaporization device and is uncompressed when suction is removed from the fluid ejection and vaporization device and an air operated flapper that pivots on a hinge as air flows through the fluid ejection and vaporization device, the air operated flapper having a biasing spring for causing the sweeping motion of the wiper blade over the ejection head when the air flow ceases through the fluid ejection and vaporization device, and causing a flow of air through the fluid ejection and vaporization device in an amount sufficient to cause movement of the wiper blade reciprocate from a first position to a second position across the ejection head.

9. The method of claim 8, wherein the air operated mechanism is biased in order to return the wiper blade to the first position from the second position when the flow of air ceases.

10. The method of claim 8, wherein the air operated mechanism comprises the air operated flapper and the biasing spring for biasing the air flapper to the first position.

11. The method of claim 8, wherein air is caused to flow through the fluid ejection and vaporization device by inhaling vapors generated by the fluid ejection and vaporization device.

12. The method of claim 8, wherein the air operated mechanism is disposed on a mouthpiece side of the vaporizing heater between the vaporizing heater and mouthpiece of the fluid ejection and vaporization device.

13. The method of claim 8, wherein the fluid ejection and vaporization device comprises an electronic cigarette.

* * * * *